(12) United States Patent
Grier et al.

(10) Patent No.: US 8,766,169 B2
(45) Date of Patent: Jul. 1, 2014

(54) SORTING COLLOIDAL PARTICLES INTO MULTIPLE CHANNELS WITH OPTICAL FORCES: PRISMATIC OPTICAL FRACTIONATION

(75) Inventors: David G. Grier, New York, NY (US); Ke Xiao, Elmhurst, NY (US)

(73) Assignee: New York University, New York, NY (US)

( * ) Notice: Subject to any disclaimer, the term of this patent is extended or adjusted under 35 U.S.C. 154(b) by 183 days.

(21) Appl. No.: 13/518,138

(22) PCT Filed: Dec. 21, 2010

(86) PCT No.: PCT/US2010/061617
§ 371 (c)(1),
(2), (4) Date: Jun. 21, 2012

(87) PCT Pub. No.: WO2011/079139
PCT Pub. Date: Jun. 30, 2011

(65) Prior Publication Data
US 2012/0273664 A1   Nov. 1, 2012

Related U.S. Application Data

(60) Provisional application No. 61/289,177, filed on Dec. 22, 2009.

(51) Int. Cl.
*G01N 21/63* (2006.01)
*G01N 35/08* (2006.01)
*H01J 40/14* (2006.01)

(52) U.S. Cl.
USPC ........ 250/251; 250/222.2; 356/335; 356/340; 356/441; 209/12.1; 209/13.1; 209/143; 210/672; 210/767

(58) Field of Classification Search
USPC .............. 250/222.2, 251, 526, 573, 574, 576; 356/256, 335, 345, 436, 441; 209/1–4, 209/12.1, 13, 16, 24, 26, 127.2, 132, 134, 209/136, 143, 155–157; 210/659, 672, 767, 210/806
See application file for complete search history.

(56) References Cited

U.S. PATENT DOCUMENTS

| | | | | |
|---|---|---|---|---|
| 5,939,716 A | * | 8/1999 | Neal .............................. | 250/251 |
| 6,055,106 A | * | 4/2000 | Grier et al. .................... | 359/566 |

(Continued)

FOREIGN PATENT DOCUMENTS

| | | |
|---|---|---|
| JP | 2005 502482 | 1/2005 |
| JP | 2008-529063 | 7/2008 |

(Continued)

OTHER PUBLICATIONS

PCT Written Opinion of the International Searching Authority, dated Aug. 31, 2011, PCT Appln. No. PCT/US2010/061617, 5 pages.

(Continued)

*Primary Examiner* — Bernard E Souw
(74) *Attorney, Agent, or Firm* — Foley & Lardner LLP (57) ABSTRACT

A method and system for controlled fractionation of particles. A sample having a plurality of particles of different size distributions. A uniform array for the preparing of optical traps having a selected array lattice constant. The plurality of particles for inputting the plurality of particles to the uniform array of optical traps at a driving direction angle $\Theta$ and the plurality of particles separating along different directions $\Theta_v$ based on variable particle attributes.

20 Claims, 6 Drawing Sheets

(56) References Cited

U.S. PATENT DOCUMENTS

| | | | |
|---|---|---|---|
| 6,797,942 B2* | 9/2004 | Grier et al. | 250/251 |
| 6,815,664 B2 | 11/2004 | Wang et al. | |
| 6,995,351 B2 | 2/2006 | Curtis et al. | |
| 7,161,140 B2* | 1/2007 | Grier et al. | 250/251 |
| 7,276,170 B2 | 10/2007 | Oakley et al. | |
| 7,324,282 B2* | 1/2008 | Grier et al. | 359/573 |
| 7,351,953 B2* | 4/2008 | Grier et al. | 250/251 |
| 7,482,577 B2* | 1/2009 | Gruber et al. | 250/251 |
| 8,128,242 B2* | 3/2012 | Grier et al. | 359/614 |
| 2003/0007894 A1* | 1/2003 | Wang et al. | 422/82.05 |
| 2003/0047676 A1* | 3/2003 | Grier et al. | 250/251 |
| 2004/0058455 A1* | 3/2004 | Grier et al. | 436/518 |
| 2007/0091442 A1* | 4/2007 | MacDonald et al. | 359/614 |

FOREIGN PATENT DOCUMENTS

| | | |
|---|---|---|
| JP | 2008 530981 | 8/2008 |
| WO | WO 03/024163 A1 | 3/2003 |

OTHER PUBLICATIONS

Ashkin, A., et al, "Observation of as single-beam gradient force optical trap for dielectric particles", Optics Letters, vol. 11 No. 5, Optical Society of America, pp. 288-290, May 1986.

Cheong, F.C., et al, "Technical note: Characterizing individual milk fat globules with holographic video microscopy", Journal of Dairy Science, vol. 92, No. 1, American Dairy Science Association, pp. 95-99 (2009).

Cheong, Fook Chiong, et al, "Flow visualization and flow cytometry with holographic video microscopy", Optics Express, vol. 17, No. 15, Optical Society of America, pp. 13071-13079, Jul. 20, 2009.

Dufresne, Eric. et. al., "Optical tweezer arrays and optical substrates created with diffractive optics", American Institute of Physics, Rev. Sci. Instrum., vol. 69, No. 5 (1998), pp. 1974-1977.

Duffy, David C., et al, "Rapid Prototyping of Microfluidic Systems in Poly(dimethylsiloxane)", Analytical Chemistry, vol. 70, No. 23, American Chemical Society, pp. 4974-4984 (1998).

Gleeson, James P., et al, "Analytical approach to sorting in periodic and random potentials", Physical Review E 73, 9 pages (2006).

Gopinathan, Ajay, et al, "Statistically Locked-In Transport through Periodic Potential Landscapes", Physical Review Letters, vol. 92 No. 13, The American Physical Society, pp. 130602-1 through 130602-4, Apr. 2, 2004.

Grier, David G., "A revolution in optical manipulation", Nature, vol. 424, Nature Publishing Group, pp. 810-816 Aug. 14, 2003.

Herrmann, John, et al "Separation of suspended particles in microfluidic systems by directional-locking in periodic fields", 23 pages, Apr. 16, 2009.

Hirai, Al, et al., "Laser Photophoresis of a Single Object Droplet in Oil in Water Emulsions", Depart of Chemistry, Osaka University (1996), pp. 5570-5575.

Korda, Pamela T, et al, "Kinetically Locked-In Colloidal Transport in an Array of Optical Tweezers", Physical Review Letters, The American Physical Society, vol. 89, No. 12, pp. 128301-1 through 128301-4, Sep. 16, 2002.

Lacasta, et al., "Sorting mesoscopic particles driven through periodic potential landscapes", Modern Physics Letters B, vol. 20, No. 23 (2006) pp. 1427-1442.

Ladavac, K. et al., "Sorting mesoscopic objects with periodic potential landscapes: Optical fractionation", Physical Review E 70, pp. 010901-1 through 010901-4 (2004).

Lee, Sang-Hyuk, et al, "Characterizing and tracking single colloidal particles with video holographic microscopy", Optical Express, vol. 15, No. 26, Optical Society of America, pp. 18275 through 18282, Dec. 24, 2007.

Lee, Sang-Hyuk, et al, "Holographic microscopy of holographically trapped three-dimensional structures", Optics Express, vol. 15, No. 4, Optical Society of America, pp. 1505-1512, Feb. 19, 2007.

Macdonald, M.P., et al, "Microfluidic sorting in an optical lattice", Nature, vol. 426, pp. 421-424, Nov. 27, 2003.

Milne, Graham, et al, "Fractionation of polydisperse colloid with acousto-optically generated potential energy landscapes", Optics Letters, vol. 32 No. 9, pp. 1144-1146, May 1, 2007.

Pelton, Matthew, et al., "Transport and Fractionation in Periodic Potential-Energy Landscapes", Grier Group Publications, Phys, Rev. E 70, 010901(R) (2004), 21 pages.

Polin, Marco, et al, "Optimized holographic optical traps", Optics Express, vol. 13, No. 15, pp. 5831-5845, Jul. 25, 2005.

Roichman, Yael, et al, "Colloidal transport through optical tweezer arrays", Physical Review E 75, 011407, 4 pages (2007).

Roichman, Yael, et al, "Optical traps with geometric abberations", Applied Optics, vol. 45, No. 15, pp. 3425-3429, May 20, 2006.

Roichman, Yohai, et al, "Optical Forces Arising from Phase Gradients". Physical Review Letters 100, 031602, 4 pages, Jan. 11, 2008.

Roichman, Yohai, et al, "Volumetric imaging of holographic optical traps", Optics Express, vol. 14, No. 22, pp. 10907-10912, Oct. 30, 2006.

Sheng, Jian, et al, "Digital holographic microscope for measuring three-dimensional particle distributions and motions", Applied Optics, vol. 45, No. 16, pp. 3893-3901, Jun. 1, 2006.

Notice of Reasons for Rejection, JP Appl. No. 2012-546160, dated Sep. 3, 2013, 6 pages.

Sancho, J M, et al., "Particle Separation by External Fields on Periodic Surfaces", Journal of Physics, Condensed Matter, SF4151-SF4163, (2005).

PCT International Search Report, dated Aug. 31, 2011, PCT Appln. No. PCT/US2010/061617, 9 pages.

Xiao et al., "Sorting Colloidal Particles into Multiple Channels with Optical Forces: Prismatic Optical Fractionation", *Phys. Rev.*, Nov. 30, 2010, pp. 051407(1-9), E82, Issue 5, USA.

* cited by examiner

SORTING COLLOIDAL PARTICLES INTO MULTIPLE CHANNELS WITH OPTICAL FORCES: PRISMATIC OPTICAL FRACTIONATION

This work was supported in part by the National Science Foundation through Grant No. DMR-0855741. The U.S. Government has certain rights pursuant to this Grant.

CROSS-REFERENCE TO RELATED APPLICATIONS

The present application is a U.S. national stage application claiming the benefit of International Application No. PCT/US2010/061617, filed on Dec. 21, 2010, which claims priority from U.S. Provisional Application No. 61/289,177, filed Dec. 22, 2009, the entire contents of which are incorporated herein by reference in their entirety.

The present invention is directed to an improved method and system for controlled fractionation of particles. More particularly, the invention is directed to a method and system for sorting colloidal and other particles by prismatic optical fractionation.

BACKGROUND OF THE INVENTION

The motion of a driven Brownian object in a periodic force field has been studied extensively for half a century, not only because of its intrinsic interest, but also because of its close relationship to such disparate physical phenomena as charge transport in Josephson junctions and the kinetics of chemical reactions. Most studies have focused on biased diffusion in one-dimensional systems, the tilted washboard problem providing the archetype for the field. Even this much-studied model continues to yield surprises, with giant enhancement of thermal fluctuations recently having been discovered for particles that are marginally trapped by the washboard.

Higher-dimensional systems have a substantially richer phenomenology because the driven particle enjoys the additional freedom of selecting its course through the force landscape. The force field itself can have a richer variety of characteristics including multidimensional symmetries and solenoidal components that give rise to interesting non-equilibrium effects. Because the particle can move around obstacles, the force landscape can even consist of impenetrable barriers. How a Brownian particle finds its way through such structured terrains remains incompletely understood.

SUMMARY OF THE INVENTION

Prismatic optical fractionation provides a practical method to sort colloidal particles that offers highly advantageous resolution and previously unavailable sorting modalities. Design criteria are provided for optical landscapes that implement specific sorting protocols and reveal ramifications of practical departures from idealized models. The following drawings illustrate selected aspects of preferred embodiments which are described in more detail hereinafter.

BRIEF DESCRIPTION OF THE DRAWINGS

FIGS. 3A(1)-3C(3) show high resolution optical fractionation of monodisperse colloidal silica spheres illustrated in terms of probability density $\rho$ ($a_p$, $n_p$) for particles of radius $a_p$ and refractive index $n_p$; and FIG. 3A(1) shows biodisperse silica particles for an input distribution; FIG. 3A(2) shows the distribution of the silica along the [11] direction; and FIG. 3A(3) shows the distribution deflected to the apex along the [10] direction; FIG. 3B(1) shows the distribution of a monodisperse silica sample separated into a smaller low index fraction in the input region; FIG. 3B(2) shows a larger, high index particle fraction in the sides region; and FIG. 3B(3) shows distribution in the apex region with the dashed curve the marginally locked in condition $n_c(a_p)$ for the array along the [10] direction (note: plotted squares are circles in each of 3B(1), 3B(2) and 3B(3) which indicate the properties of four representative spheres whose trajectories are plotted in FIG. 2B); and FIG. 3C(1) shows a monodisperse polystyrene sample distribution at the input region; FIG. 3C(2) shows the sides distribution along the [11] direction and FIG. 3C(3) shows the distribution deflected to the apex along the [10] direction;

A color rendering of FIG. 5A shows prismatic optical fractionation computed probability density of particles colored by locked-in direction of trajectory through the optical trap array; the output was divided into four directional categories: [10], [21], [31] and undeflected; and individual traps appear as local probability maxima; and a color rendering of FIG. 5B shows a map of particle properties $a_p$ and $n_p$ colored by mean transport direction through the array. Red: [10], Green: [21], Cyan: [31], Blue: undeflected.

DETAILED DESCRIPTION OF PREFERRED EMBODIMENTS

In one preferred form of the invention an optical trap is modeled as a potential energy well for a colloidal particle.

The optical forces experienced by the colloidal particle, such as a sphere, moving through a non-uniform light field depend on the particle's radius $a_p$ and refractive index $n_p$. We model the j-th optical trap in an array of traps as a three-dimensional Gaussian well, $$V(r \mid a_p, n_p) = -V_0(a_p, n_p)\exp\left(-\frac{r^2}{2\sigma^2(a_p)}\right), \qquad (1)$$

whose depth is, $$V_0(a_p, n_p) = \frac{n_m a_p^3}{\sigma^2(a_p)c}\left(\frac{m^2-1}{m^2+2}\right)p, \qquad (2)$$

and depends on the strength of a particles' interaction with the focused light beam, and whose range depends on the particle's size through the expression, $$\sigma^2(a_p) = a_p^2 + \left(\frac{0.61\lambda}{NA}\right)^2, \qquad (3)$$

where NA is the numerical aperture of the lens that brings the light to a focus. Here, $m=n_p/n_m$ is the refractive index of the particle, $n_p$, relative to that of the medium, $n_m$, for light of vacuum wavelength $\lambda$, p is power of the laser beam powering the trap, and c is the speed of light in vacuum. An array of N identical traps centered at positions $r_j$ therefore creates a landscape, $$W(r \mid a_p, n_p) = \sum_{j=-\frac{N}{2}}^{\frac{N}{2}-1} V(r - r_j \mid a_p, n_p), \qquad (4)$$

with a total laser power P=Np whose structure depends not only on the distribution of projected light, but also on the properties of the particle passing through it.

A. Transport in a Potential Energy Landscape

A particle driven through such a potential energy landscape by the Stokes drag of a fluid of viscosity η flowing at velocity v experiences a maximum force of, $$F_0(a_p) = 6\pi\eta a_p \qquad (5)$$

in the direction of the flow. If this driving force is smaller than the maximum restoring force that a trap can exert, a particle will become localized in the first trap it encounters. To ensure that the particle moves continuously through the landscape, we therefore require:

$$F_0(a_p) > \frac{V_0(a_p, n_p)}{\sigma(a_p)\sqrt{e}} \qquad (6)$$

Small particles also are influenced by random thermal forces that tend to help them to escape from traps. Such thermally activated processes can be used to sort microscopic objects, albeit quite slowly. The influence of thermal fluctuations can be minimized by ensuring, $$V_0(a_p, n_p) > k_B T \qquad (7)$$

at absolute temperature T. This, together with Eq. (6) describes particles moving rapidly through an array of traps, which is the appropriate limit for high-throughput sorting. The particle's most likely trajectory then can be computed with deterministic equations of motion. Even in this limit, thermal fluctuations can influence a particle's trajectory, as will be discussed in Sec. II E hereinafter.

B. Transport Through a Line of Traps

The driving force may be oriented at angle $\Delta\Theta_\nu$ with respect to a symmetry direction $\hat{x}_\nu$ through the landscape, labeled by index v. If the particle hugs the landscape and moves along $\hat{x}_\nu$ rather than following the applied force, it is said to be kinetically locked-in to that direction. For this to happen, the particle must be deflected enough by its interaction with one trap to enter into the potential energy well of the next. In particular, the total force exerted by the traps must be large enough to compensate for the driving force along $\hat{y}_\nu$, the direction perpendicular to $\hat{x}_\nu$.

If we assume that the traps are arranged periodically, $r_j = jb_\nu \hat{x}_\nu$ with lattice constant $b_\nu$, the transverse force is, $$F_y = -\frac{V_0}{\sigma(a_p)}\frac{y_\nu}{\sigma(a_p)}\exp\left(-\frac{y_\nu^2}{2\sigma^2(a_p)}\right)\sum_{j=-\frac{N}{2}}^{\frac{N}{2}-1}\exp\left(-\frac{(x_\nu - jb)^2}{2\sigma^2(a_p)}\right) + \qquad (8)$$

$$F_0(a_p)\sin\Delta\Theta_\nu$$

and this transverse force must vanish for the particle to remain kinetically locked-in at deflection angle $\Delta\Theta_\nu$. The maximum deflection angle therefore satisfies:

$$\sin\Delta\Theta_\nu \leq \frac{V_0(a_p, n_p)}{\sigma(a_p)F_0(a_p)}\frac{y_\nu}{\sigma(a_p)}\exp\left(-\frac{y_\nu^2}{2\sigma^2(a_p)}\right)\sum_{j=-\frac{N}{2}}^{\frac{N}{2}-1}\exp\left(-\frac{(x_\nu - jb_\nu)^2}{2\sigma^2(a_p)}\right) \qquad (9)$$

along the entire trajectory $r(t)=(x_\nu(t), y_\nu(t))$ observed in the $(\hat{x}_\nu, \hat{y}_\nu)$ frame. The deflection angle is limited by the maximum transverse force that the landscape can apply, which occurs at $y_\nu = \sigma(a_p)$. Particles must remained locked-in, furthermore, along the entire length of the array, including the midpoints between the traps which are its weakest points. If we assume that the transverse force is dominated by the two nearest traps, we recover the result, $$\sin\Delta\Theta_\nu \leq \frac{V_0(a_p, n_p)}{\sigma(a_p)F_0(a_p)}\frac{2}{\sqrt{e}}\exp\left(-\frac{b_\nu^2}{8\sigma^2(a_p)}\right) \qquad (10)$$

This is an underestimate for the maximum deflection angle because it does not include contributions from more distant traps. For an infinite array, $$\sin\Delta\Theta_\nu \leq \frac{V_0(a_p, n_p)}{b_\nu F_0(a_p)}\sqrt{\frac{2\pi}{e}}\,\vartheta_3\left(-\frac{\pi}{2}, \exp\left(-\frac{2\pi^2\sigma^2(a_p)}{b_\nu^2}\right)\right), \qquad (11)$$

where $\vartheta_3(\ldots)$ is an elliptic theta function, always exceeds the prediction of Eq. (10). Furthermore, $y_\nu = \sigma$ may not be kinematically accessible at the midline between the traps because no periodic trajectory reaches there. In that case, particles would remain kinetically locked-in to the $\hat{x}_v$ direction at steeper angles without falling through the 'holes' between the traps. On the other hand, the derivation of Eq. (10) does not account for thermal fluctuations or randomness in the position and depth of the traps, both of which help particles to break free of locked-in trajectories. Stably locked-in transport therefore might be limited to angles smaller than predicted by Eq. (10).

C. Two-Dimensional Kinetic Lock-in

Although Eq. (10) was derived for transport along one-dimensional arrays of traps, it provides useful insights also into transport through two-dimensional arrays. A given lattice of traps possesses symmetry directions described by Miller indexes v=[ij]. These directions are oriented at angles $\Theta_v$ with respect to the array's principal lattice direction. The driving force $F_0$ is oriented at angle $\Theta$ with respect to the axis. The particle's trajectory then passes through the array at an angle that we label $\phi$. In order to determine colloidal transport through two-dimensional arrays one must determine how $\phi$ depends on the properties of the particle and the array for a given driving direction $\Theta$.

A particle should become locked-in to direction v if the driving force is oriented within $\Delta\Theta_v$ of $\Theta_v$. The maximum deflection angle, $\Delta\Theta_v$, depends on the array's geometry through the inter-trap separation, $b_v$. For example, a square array with lattice constant b has separations $$b_v = b\sqrt{i^2+j^2}$$ and for 3D, it is $$b_v = b\sqrt{i^2+j^2+k^2}.$$

Figure 1:
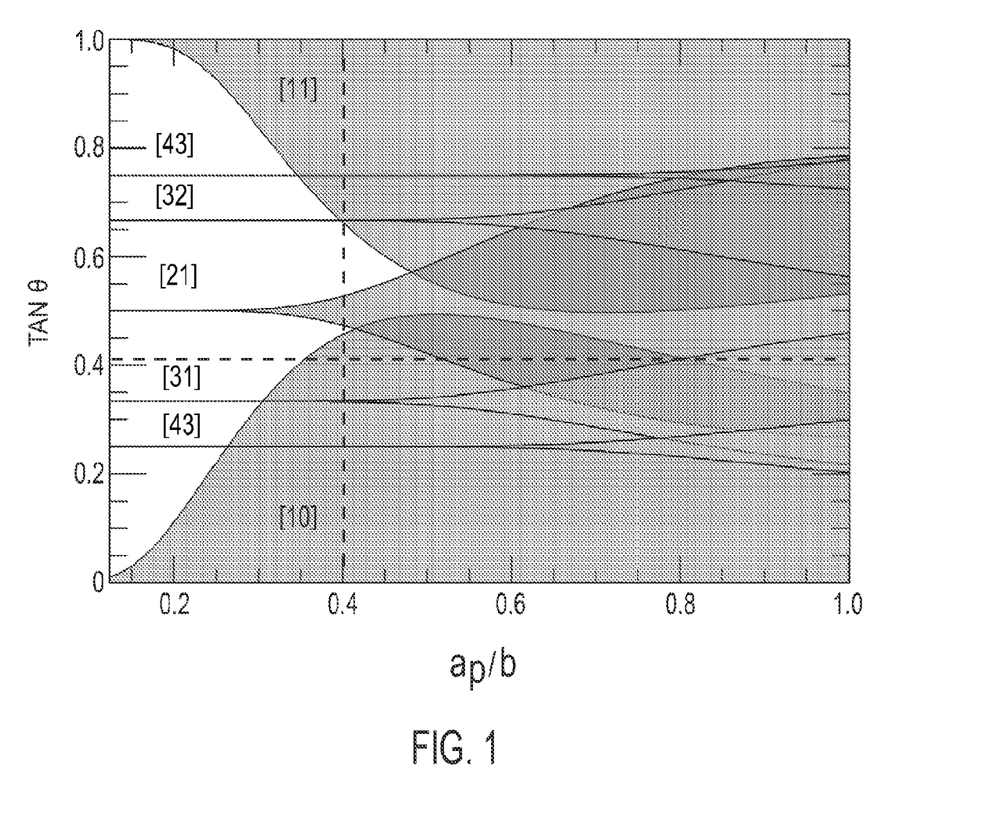
FIG. 1 shows locked-in directions as a function of particle size for a sphere of fixed refractive index $n_p$ moving under a constant force $F_0$ ($a_p$, $n_p$) at angle $\Theta$ through a square trap array.

The range of locked-in angles around a given direction $\Theta_v$ therefore falls off rapidly with increasing index v. FIG. 1 depicts this transport characteristic for a few illustrative directions through a square array as a function of particle size for a fixed refractive index and laser power. Shaded regions in FIG. 1 indicate predictions of Eq. (11) for the conditions under which a sphere of radius $a_p$ becomes kinetically locked-in to particular lattice directions indicated by their Miller indices. Overlapping regions indicate opportunities for statistically locked-in transport, with higher-index directions becoming accessible as random sequences of lower index jumps. Unshaded regions indicate conditions under which the particle freely follows the direction of the driving force. The horizontal dashed line indicates the different fates of particles with different sizes moving through a square lattice at fixed orientation tan $\Theta$=0.41. The vertical dashed line indicates the lock-in transitions that a particle of radius $a_p$=0.4b will experience as the driving direction is rotated from $\Theta$=0° to $\Theta$=45°.

D. Lock-in Transitions

A particle driven at an angle $\Theta$ that falls into one of the unshaded regions in FIG. 1 is not locked in to any direction according to Eq. (10). Consequently, it is not systematically deflected by the array and travels along the driving direction with $\phi=\Theta$.

If, on the other hand, the particle falls into the locked-in domain around symmetry direction $\Theta_v$, its trajectory is deflected away from the driving direction $\Theta$ and the particle travels instead along $\phi=\Theta_v$. The vertical dashed line in FIG. 1 therefore maps out the fate of a given size and composition of particle as a function of driving direction. For a given driving direction, the particle either is locked-in to nearest symmetry of the lattice or else escapes from the lattice and travels in the direction of the driving force.

E. Statistically Locked-in Transport

The situation is different for larger particles that interact more strongly with the lattice. In this case, the locked-in domains predicted by Eq. (11) can overlap. The higher-index directions in such overlapping regions are not microscopically accessible because particles will encounter and interact preferentially with traps along lower-index directions. Under these conditions, the particle may principally follow one direction with occasional excursions in another. The net result is a mean travel direction $\Theta$ that reflects the influence of all overlapping symmetry directions. What direction the particle travels depends on the relative probability for jumps in microscopically accessible directions which may require a full two-dimensional treatment to determine.

The overlap in the one-dimensional results still has predictive power in that it signals a cross-over from deterministically locked-in transport along the low-index direction to statistically locked-in transport along another direction. This becomes still more complicated when locked-in domains for multiple lattice directions overlap.

The resulting competition between candidate locked-in directions at least qualitatively explains the fairly complicated pattern of locked-in plateaus that have been reported experimentally for colloidal transport through square arrays of traps.

F. Prismatic Optical Fractionation

Although the angles $\Theta_v$ are defined solely by the geometry of the array, the ranges $\Delta\Theta_{v_j}$ depend also on other attributes, particularly the size and refractive index of the particle that interacts with the optical and potential energy field character of the array of traps. Thus, in a preferred embodiment, for a given driving orientation $\Theta$, therefore, different objects may travel in different directions $\phi_i$ as a function of attributes, such as, at least one of particle size $a_p$ and index of refraction, $n_p$. This effect may be used to sort objects into spatially separated fractions on the basis of their physical properties, a process known as optical fractionation. Previous realizations of optical fractionation have sorted samples into two fractions usually distinguished by whether or not particles were locked in to a particular direction. Sorting into more fractions or more refined fractions then relied on passing samples through multiple gradated stages of optical force fields. The possibility that different objects might become kinetically locked-in to different directions in a uniform, static landscape has been proposed as a useful means to implement multi-channel optical fractionation. How this might be accomplished in practice has not been specified or explained.

The horizontal dashed line in FIG. 1 indicates one strategy for sorting into multiple fractions by size with a single pass through a uniform array of optical traps. Particles too small to be locked in to any lattice direction travel through the array undeflected, with $\phi=\Theta$. Other somewhat larger particles satisfy $\Theta \leq \Delta\Theta_{[10]}$ and become kinetically locked in to $\phi=0°$. Still larger particles become statistically locked in to $\phi=\Theta_{[21]}$ and are deflected in the opposite direction to $\phi=27°$. The sample thus is divided by size into three distinct fractions whose physical separation scales linearly with the size of the optical trapping array. The size ranges in each fraction can be tuned through the driving angle and the array's lattice constant. Such simultaneous sorting into multiple distinct channels distinguishes prismatic optical fractionation from other modes of operation.

In one example embodiment, we can further refine this treatment for optical fractionation of spheres by sorting on the basis of (complex) refractive index as well as size. Equation (10) may be recast to differentiate those particles that can become locked in to a particular direction at a specific driving angle from those that cannot:

$$n_v(a_p)n_m \sqrt{\frac{A(a_p) + 2B_v(0)}{A(a_p) - B_v(\Theta)}}, \text{ where} \quad (12)$$

$$A(a_p) = \left(\frac{a_p}{b}\right)^2 \left(\frac{b}{\sigma_p}\right)^3 \exp\left(-\frac{b^2}{8\sigma_p^2}\right) \quad (13)$$

depends on particle size through the ratio $a_p/b$, and $$B_v(\Theta) = \frac{\sqrt{e}}{2} \frac{6\pi \eta v c}{n_m P} b \sin(\Theta - \Theta_v). \quad (14)$$

Particles satisfying $n_p \geq n_v(a_p)$ can become locked-in to the lattice direction at angle $\Theta_v$, and those with $n_p < n_v(a_p)$ should escape.

In considering these results for practical applications, some account should be taken of the underlying approximations. Even if the more comprehensive Eq. (11) is substituted for Eq. (10), the forms for $V_0(a_p, n_p)$ and $\sigma(a_p)$ in Eqs. (2) and (3) are approximate, particularly for particles comparable in size to the wavelength of light or larger.

III. EXAMPLES

The following non limiting examples illustrate various non-limiting experimental aspects of preferred embodiments of the invention.

Figure 2A:
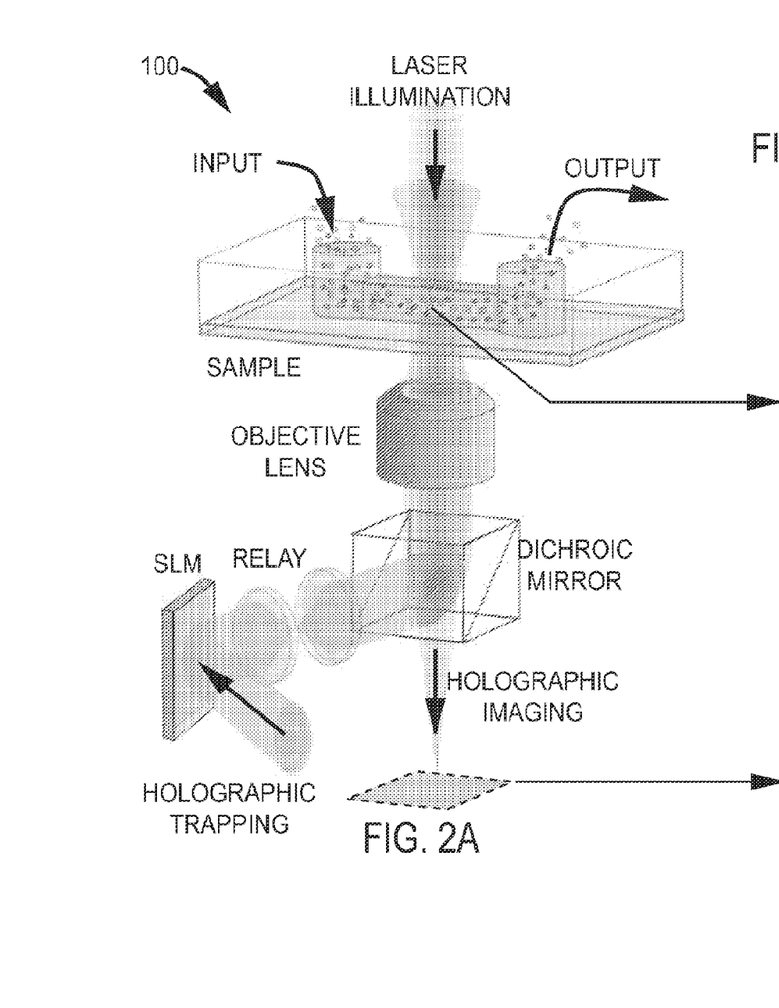
FIG. 2A shows a combined holographic optical trapping and holographic video microscope system for tracking and characterizing particles during optical fractionation.

The theory outlined above performs remarkably well in describing and predicting the outcome of experimental fractionation studies performed. Experimental implementation is shown schematically in FIG. 2A by system 100. Colloidal spheres dispersed in deionized water flow through a 2 cm long microfluidic channel with a 1 mm×30 μm rectangular cross-section. The channel is cast in poly(dimethyl siloxane) (PDMS) and bonded to a no. 1.5 glass cover slip and the constant flow is maintained with a syringe pump (Harvard Apparatus PHD 2000).

Figure 2B:
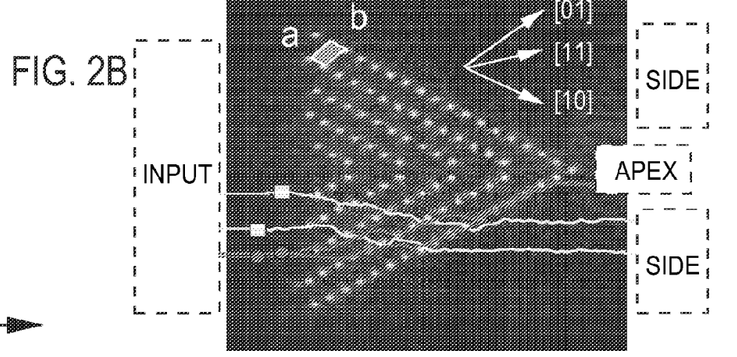
FIG. 2B shows an image of 103 holographic optical tweezers taken in the focal plane of the microscope of FIG. 2A and also shows trajectories of particles.

This sample is mounted on the stage of an inverted optical microscope (Nikon TE2000U) outfitted with a 100× oil-immersion objective (Nikon Plan Apo, NA=1.4). This objective lens is used to project arrays of optical tweezers into the midplane of the sample using the holographic optical trapping technique. FIG. 2B shows the measured intensity of a typical optical trap array recorded in the microscope's focal plane, each discrete optical tweezer appearing as a point of light. This optical trap array is powered by a frequency-doubled solid state laser (Coherent Verdi 5W) operating at a vacuum wavelength of $\lambda$=532 nm whose beam is imprinted with computer-generated holograms using a liquid crystal spatial light modulator (SLM) (Hamamatsu X8267-16). The hologram then is relayed to the objective lens' input pupil with a dichroic mirror.

Figure 2C:
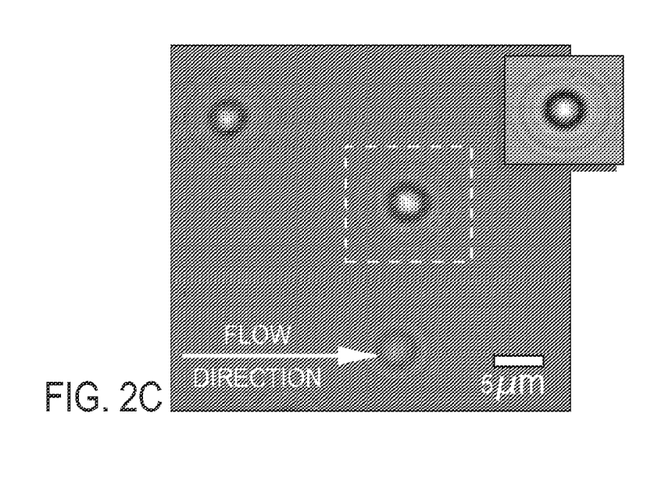
FIG. 2C shows a normalized holographic image of 1.5 µm diameter silica spheres in the same field of view of FIG. 2B with an insert image (upper right) showing a fit to the Lorenz-Mie theory of the outlined sphere's holographic image.

The sample also is illuminated with the collimated beam from a HeNe laser (Uniphase 1103P) operating at a vacuum wavelength of 632.8 nm. Light scattered by the colloidal spheres interferes with the unscattered portion of the beam in the focal plane of the objective lens. The interference pattern is collected by the objective lens and relayed by a video eyepiece to a video camera (NEC TI-32411A) that records its intensity at 30 frames/s. This system has an effective magnification of 0.091 μm/pixel. FIG. 2C shows a typical holographic snapshot of colloidal spheres interacting with the optical trap array in the same field of view as FIG. 2B.

We fit each sphere's holographic image to predictions of the Lorenz-Mie theory of light scattering using the MPFIT implementation of the Levenberg-Marquardt nonlinear least-squares fitting algorithm. Each fit yields a sphere's three-dimensional position with nanometer resolution and also its radius with nanometer resolution and its complex refractive index to within one part in a thousand. A typical fit is shown in the inset to FIG. 2C. This approach to holographic video microscopy therefore provides the time-resolved tracking and characterization data required to assess the efficacy of arrays of optical tweezers to sort fluid-borne particles through kinetically and statistically locked-in transport.

Example A

Mixed Silica Colloidal Particles

Figure 3A:
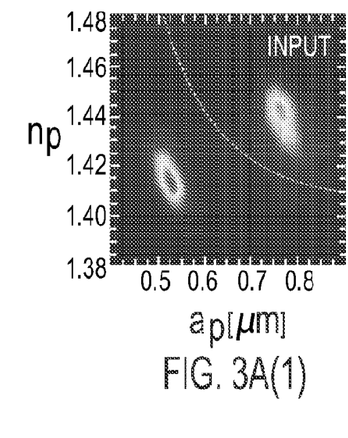
Figure 3B:
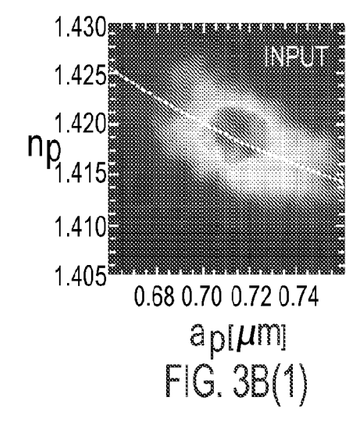
Figure 3C:
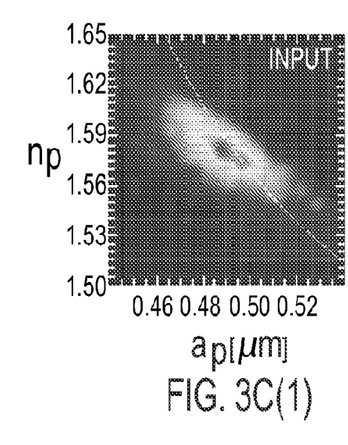

The data in FIGS. 3A(1)-3A(3) show results obtained with a mixture of two populations of monodisperse colloidal silica spheres, one 1.0 μm in diameter (Duke Scientific Catalog #8100, Lot #21024) and the other 1.5 μm diameter (Duke Scientific Catalog #8150, Lot #30158) at 1:1 stoichiometry. This mixed dispersion was owed at v=24±8 μm=s, through an optical trap array of the type shown in FIG. 2B with inter-trap separation of b=2.025 μm along the [10] direction and a=3.27 μm along the [01] direction. The [10] direction is inclined at $\Theta$=30° with respect to the flow. The laser power per trap is estimated to be P=2.0±0.3 mW/trap based on imaging photometry of images such as the one in FIG. 2B.

The dense silica spheres tend to settle to the lower wall of the channel, as confirmed by three-dimensional holographic particle tracking. They thus approach the trap array more slowly than the peak flow rate along the channel's midplane because of the Poiseuille flow profile. Once they encounter the traps, however, they are drawn to the midplane by optical forces, and move through the array in the peak flow. This focusing of the colloidal flow by optical forces was overlooked in previous studies and helps to explain why an idealized two dimensional analysis might be successful at explaining transport through a complex highly structured three-dimensional optical field.

Under these conditions, Eq. (12) predicts that the larger spheres will be locked-in to the [10] direction while the smaller spheres will be statistically locked-in to [21]. The dividing line based on this prediction is plotted as a dashed curve in the $n_p(a_p)$ plane in FIGS. 3A(1)-3A(3) and passes cleanly between the two populations.

A random sample of 2500 particles passing through the input region (indicated in FIG. 2B) was characterized by Lorenz-Mie scattering theory. These particles radii, $a_p$, and refractive indexes, $n_p$, were compiled with a non-parametric density estimator into the relative probability distribution $\rho(a_p, n_p)$ plotted in FIGS. 3A(1)-3A(3). This clearly resolves the two populations of silica spheres, the larger of which is slightly less dense than the smaller. The marked anticorrelation between size and refractive index in the individual monodisperse populations appears to be a normal feature of particles synthesized by emulsion polymerization and is not seen in samples of known uniform density such as fluid droplets. This input distribution passed through the array of optical tweezers and into the two analysis regions indicated in FIG. 2B, one at the apex at the array and the other comprised of the two side regions. These two output distributions, plotted in FIG. 3A(3) show that the large particles are preferentially deflected to the apex of the array whereas the smaller particles are preferentially deflected to the sides. A small proportion of the large spheres did not become locked-in to the direction or otherwise leaked through the array and so appear in the side distribution. Similarly small particles that entered the array near its midline were not deflected and passed through to the apex. A larger proportion of small spheres thus contaminates the distribution analyzed at the apex. Even so, the two populations were sorted with better than 90% efficiency in the side distribution and better than 80% efficiency at the apex.

Previous studies have demonstrated optical fractionation of bidisperse colloidal mixtures with such easily distinguishable characteristics. Theoretical studies suggest that optical fractionation can have exquisitely fine resolution for sorting by size, and perhaps by refractive index. Although these predictions have been tested indirectly through transport studies on monodisperse samples, Lorenz-Mie characterization has fine enough resolution for particle size and refractive index to enable direct tests.

Example B

Monodisperse Silica Colloidal Particles

FIGS. 3B(1)-3B(3) show comparable results in the same optical tweezer array for a monodisperse sample of colloidal silica spheres with a nominal radius of 0.75±0.04 µm (Poly-Sciences Catalog #24327, Lot #600424). Lorenz-Mie characterization reveals the actual sample-averaged radius to be somewhat smaller and more sharply distributed than the manufacturer's specification, with $a_p$=0.715±0.021 µm. The measured refractive index of $n_p$=1.418±0.004 also is significantly lower than the nominal range for 1.43 to 1.46 for colloidal silica spheres, suggesting that these spheres are somewhat porous.

This sample was flowed with a slightly lower speed, $v$=22±5 µm/s, than in the previous example so that the predicted condition for locked-in transport along cuts through the middle of the sample's range of properties. The results in FIGS. 3B(1)-3B(3) show that smaller particles with lower refractive index are systematically deflected into the side areas, their mean deflection indicating statistically locked-in transport along. The larger higher-index particles, by contrast, are kinetically locked-in along and are deflected to the apex of the array. These distributions were obtained with 6,000 randomly selected particles. The discrete points plotted in FIGS. 3B(1) and 3B(3) indicate the properties of the four particles whose trajectories are plotted in FIG. 2B.

Although the mean radius of the particles deflected to the apex is only slightly greater than that of the other fraction (0.716±0.021 µm versus 0.710±0.027 µm), the difference is found to be statistically significant at the 99.9 percent level with a Wilcoxon rank-sum test. A far more substantial distinction is observed in the refractive indexes of the sorted populations. The spheres at the apex have a mean refractive index of 1.420±0.003 whereas the side fraction has a mean refractive index of 1.416±0.003. These two populations again differ with better than 99.9 percent confidence according to the Wilcoxon rank-sum test.

Not only do these results agree quantitatively with the predictions of Eq. (12) for kinetic lock-in along the direction, they also agree with the heuristic model of Sec. IIE for the onset of statistical lock-in. The initially monodisperse sample is thereby divided into two spatially separated fractions with resolution for refractive index approaching the part-per-thousand resolution of Lorenz-Mie characterization. To the best of our knowledge this is the finest resolution for fractionation by refractive index reported for any technique. It is achieved, moreover, despite the inevitable imperfections in the optical trap array and fluctuations in the fluid velocity. As in the previous example, the efficiency for sorting exceeds 95% in both samples.

Example C

Monodisperse Polystyrene Colloidal Particles

The data in FIGS. 3C(1)-3C(3) were obtained under comparable conditions with monodisperse samples of polystyrene spheres with a nominal radius of 0.50±0.02 µm (Duke Scientific Catalog #5100A, Lot #27527) and a nominal refractive index of 1.59 at 589 nm. Unlike silica spheres, polystyrene spheres are only 5% more dense than water. Consequently, they fill the channel as the flow toward the array of traps. Their comparatively high refractive index, moreover, renders them more susceptible to radiation pressure and thus less strongly trapped by optical tweezers. Rather than being drawn by optical forces toward the cell's midplane, consequently, these spheres predominantly are pushed toward the upper glass wall and creep along the surface in the slowest part of the Poiseuille flow. To compensate for the observed axial displacement, we refocus the optical trap array so that the particles continue to pass through in the plane of best focus. We furthermore modify Eq. (5) to account for the spheres' hydrodynamic coupling to the wall at distance h from their centers:

$$F_0(h) = -6\pi\eta a_p\left(1 - \frac{9a_p}{16h} + o\left\{\frac{a_p^3}{h^3}\right\}\right)^{-1} v. \quad (15)$$

At a measured height of $h$=(1.2±0.1)$a_p$, the particles move down the channel at $v$=7.7±2.5 µm/s.

Given these considerations, a trap array resembling that in the previous examples was created with lattice parameters b=2.5 µm and a=2.72 µm and powered with a laser power of P=2.2±0.2 mW/trap. The resulting threshold for kinetic lock-in to the [10] direction is plotted in FIGS. 3C(1)-3C(3). This array was designed so that the fastest of the most strongly interacting particles would remain kinetically locked-in. Unlike the previous demonstration of sorting of silica spheres, this array was designed to emphasize sorting by size. The slope of $n_c(a_p)$ can be adjusted with the accessible control parameters to achieve a desired balance between sorting by size and refractive index.

The data in FIGS. 3C(1)-3C(3) were amassed from the trajectories of 2,000 randomly chosen particles. Despite complications arising from the less easily trapped sample, the prediction of Eq. (12) still quantitatively agrees with the measured distributions in the two output fractions, the nominally monodisperse sample being separated into even more finely resolved fractions along the curve $n_c(a_p)$. The mean radius of the particles in the apex region, 0.497±0.017 µm, is substantially larger than in side regions, 0.478±0.014 µm, demonstrating sorting by radius with a resolution finer than 20 nm. The difference in size between the two fractions is found to be statistically significant at the 99.9 percent level with a Wilcoxon rank-sum test. Although the two fractions also differ slightly in mean refractive index (1.576±0.016 versus 1.589±0.019), this difference is only significant at the 95% confidence level. The polystyrene particles thus indeed are sorted mainly by their sizes.

Example D

Simulation Results Compared to Experimental Examples

The Langevin equation of motion for a colloidal sphere moving in flowing fluid through an optical trap array is $$\epsilon \frac{dr(t)}{dt} = -\nabla W(r) + F_0 + \Gamma(t), \quad (16)$$

where $\epsilon$ is the sphere's viscous drag coefficient, and where $\Gamma(t)$ describes random thermal fluctuations. The stochastic force satisfies $\langle \Gamma(t) \rangle = 0$ and $\langle \Gamma(t) \cdot \Gamma(t+\tau) \rangle = 2 \xi k_B T \delta(\tau)$ at temperature T, where $\delta(\tau)$ is the Dirac delta function. We integrated this equation of motion with the stochastic fourth-order Runge-Kutta algorithm to obtain simulated trajectories, r(t), that are analogous to the experimental data presented in the previous Section. Particles with sizes and refractive indexes drawn at random from a desired distribution were released at random into the force and flow fields described by Eqs. (4) and (5) respectively, and their in-plane motions compiled into distributions comparable to those obtained experimentally.

Figure 4A:
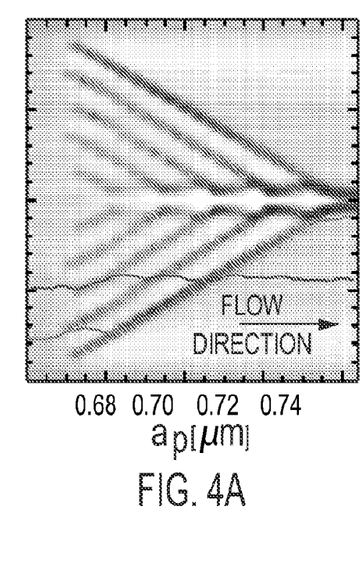
FIG. 4A shows computed probability density of particles flowing from left to right through an array.

The data in FIG. 4A-D show results of such simulation designed to mimic the experimental conditions in FIGS. 3B(1)-3B(3). Particle properties, $a_p$ and $n_p$ were selected at random from an elliptical Gaussian distribution fit to the measured input distribution in FIG. 3A(1). Each particle then was released at a random position within the input region indicated in FIG. 2B and its subsequent trajectory recorded. FIG. 4A shows the probability distribution of particle positions for 5,000 such simulated trajectories.

Figure 4B:
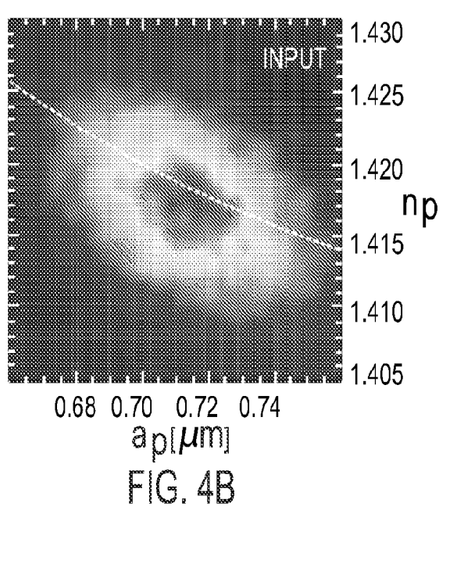
FIG. 4B shows the distribution of refractive indices and radii of spheres in the input region, and which are chosen to mimic an experimentally observed sample.

The specific distribution of input properties is plotted in FIG. 4B to permit direct comparison with the experimental size and refractive index distribution obtained with holographic video microscopy in FIGS. 3B(1)-3B(3). The dashed curve in these figures is the predicted lock-in condition for the direction through the simulated array of traps, using the experimentally determined parameters.

Figure 4C:
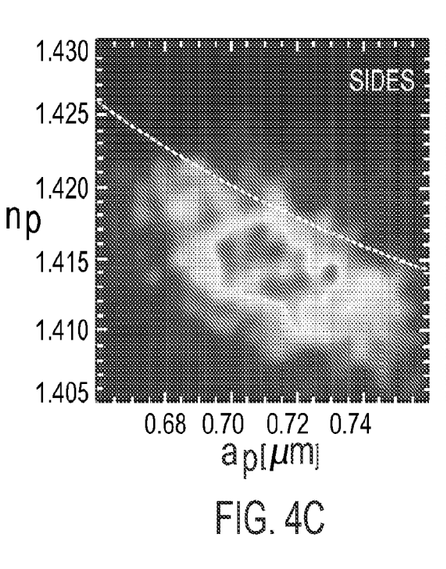
FIG. 4C shows output distribution in the side region and FIG. 4D shows output distribution in the apex region.
Figure 4D:
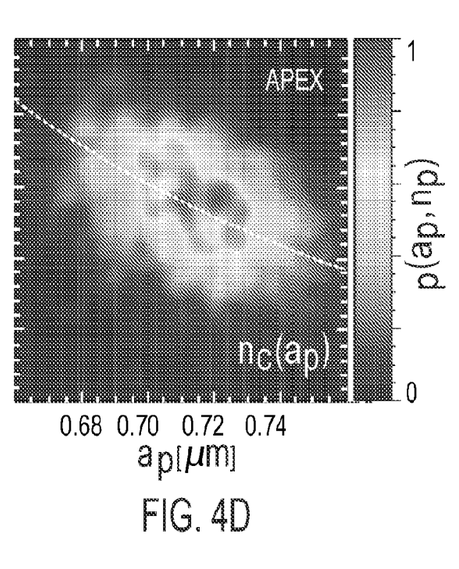

FIGS. 4C-4D show the simulated output distributions in the apex and side collection areas indicated in FIG. 2B. As for the experimental results in FIGS. 3B(1)-3B(3), the simulated trajectories yield well-sorted output fractions with the larger, more strongly interacting particles being preferentially deflected to the apex of the trapping array and the smaller more weakly interacting fraction either passing through the array or else being deflected to the side regions. As in the experimental case, the division between output fractions falls closely along the curve predicted by Eqs. (12) through (14).

These observations lend support to our suggestion that the idealized one-dimensional model developed in Sec. II quantitatively predicts the trajectories of particles moving through two-dimensional arrays of traps, including capturing the transition to statistically locked-in transport. They also suggest that the experimental results in Sec. III were correctly interpreted within this model.

Similarly good agreement between experiment, simulation and theory are obtained for the other experimental realizations as well. Optimization of prismatic fractionation can be described to elaborate on other preferred embodiments. Although prismatic optical fractionation in inclined arrays of optical tweezers is demonstrably effective in sorting colloidal spheres by size and by refractive index, the mode of operation that we have demonstrated hereinbefore is one preferred embodiment. In particular, the selected fraction at the apex is mixed with a small population of particles that were not deflected at all. This defect is obvious in the results presented in FIGS. 3A(1)-3C(3). This can be overcome at the cost of slight additional complexity, as we now demonstrate with Brownian dynamics simulations.

Figure 5A:
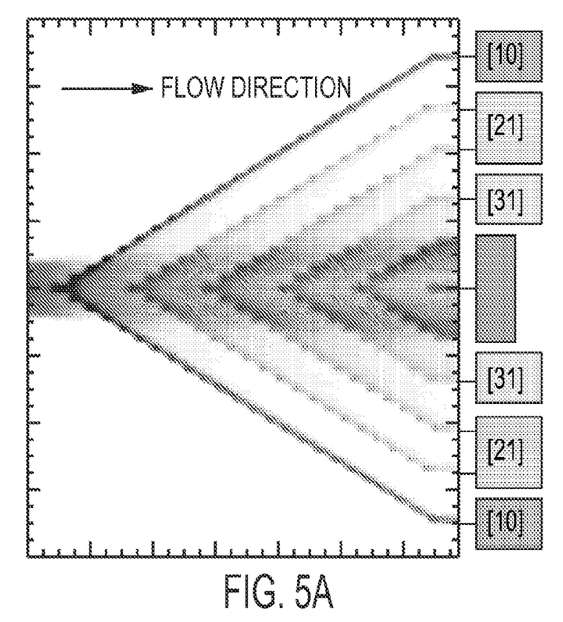
FIG. 5A shows the computed probability density of particles undergoing prismatic optical fractionation as they flow through an array of optical traps designed to implement prismatic optical fractionation. An initially mixed sample is divided into four spatially separated fractions on the basis of the size $a_p$ and refractive index $n_p$ of the particles. Different components of the initially mixed sample area divided into four directional categories: [10], [21], [31] and undeflected. Individual traps appear as local probability maxima.

The problem of spheres leaking through the array can be mitigated by reversing the flow direction and confining the incoming stream of particles to a comparatively narrow stream within the bulk flow, as shown in FIG. 5A. In practice, particles can be confined in this way with hydrodynamic flow focusing in a microfluidic chip. FIG. 5A shows the probability density for finding a particle at a given position in the plane. Individual traps in the array are visible as local probability maxima.

Regions are shaded and labeled according to the mean direction of the trajectories passing through. Trajectories along [10] direction are kinetically locked-in. Those in the [21] and [31] directions are statistically locked-in. The remaining trajectories are not substantially deflected by the array. Output bins are defined as indicated in FIG. 5A for each of these four categories.

Figure 5B:
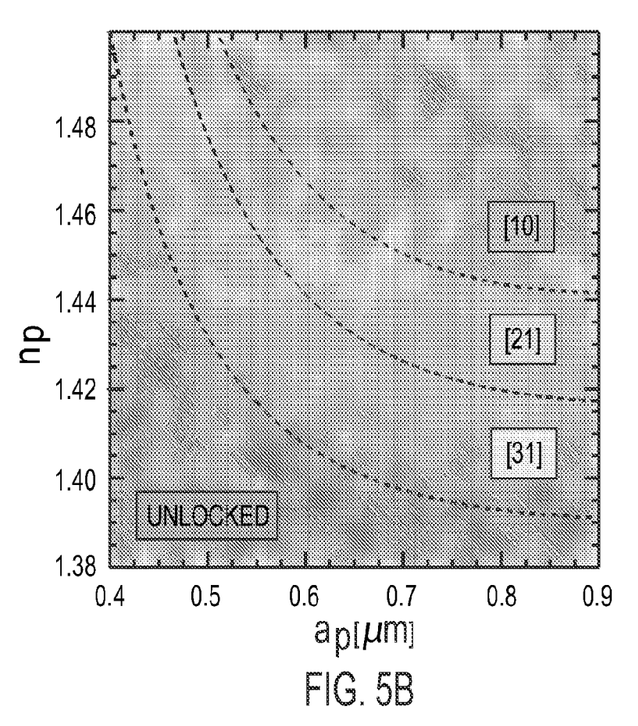
FIG. 5B shows a map of particle properties $a_p$ and $n_p$ shaded by mean transport direction through the array. Dashed curves show predicted transition boundaries between different locked-in transport conditions, in good agreement with simulation results.

Particles in these simulations were selected with the broad range of radii and refractive indexes indicated in FIG. 5B. Each point in this map indicates the mean transport direction taken by particles with those properties, using the same labeling scheme as in FIG. 5A. The space is clearly divided into bands of transport properties, with the largest, most strongly interacting particles being locked-in to the direction and the smallest, least strongly interacting particles passing through the array undeflected.

The dashed curves in FIG. 5B indicate the predictions of Eq. (12) for kinetically locked-in transport along, and statistically locked-in transport along [21] and [31]. These dashed curves agree reasonably well with the observed fates of the particles. The success of Eq. (12) at predicting the transitions to and between statistically locked-in states is quite remarkable considering its derivation from a semi-quantitative one-dimensional model. This simulation also demonstrates the possibility and potential utility of prismatic optical fractionation to sort heterogeneous samples into multiple spatially separated fractions simultaneously and continuously.

In the various embodiments of the invention a homogeneous periodic force landscape can be used to sort microscopic spheres into spatially separate fractions with extremely fine resolution for size or refractive index. Although the basis for designing such multidimensional separations, Eq. (12), was obtained using limiting arguments for a one-dimensional array, it has proved quantitatively accurate for predicting the transport of colloidal spheres through two-dimensional arrays of traps both in simulation and also experimentally. This success is observed not only for kinetically locked-in transport along microscopically accessible sites, but also for statistically locked-in transport along directions that are not microscopically accessible.

It has been demonstrated that prismatic optical fractionation can be used to select two fractions from a heterogeneous sample and to deflect them in opposite directions. Our simulations of the inverted geometry suggest that fractionation into multiple physically distinct samples also should be feasible. Such multi-channel multidimensional sorting takes advantage of both kinetically and statistically locked-in transport mechanisms.

The present embodiments focus on sorting of colloidal spheres that are well enough separated to avoid inter-particle interactions. Pairwise collisions tend to blur the transitions among locked-in states and might be expected to diminish the effectiveness of prismatic optical fractionation. Many-body cooperativity, however, might open new avenues for sorting. Recent studies have begun to extend the study of locked-in transport to aspherical objects. These also suggest avenues for continuous sorting, including so-far untapped channels for prismatic optical fractionation.

Figure 6:
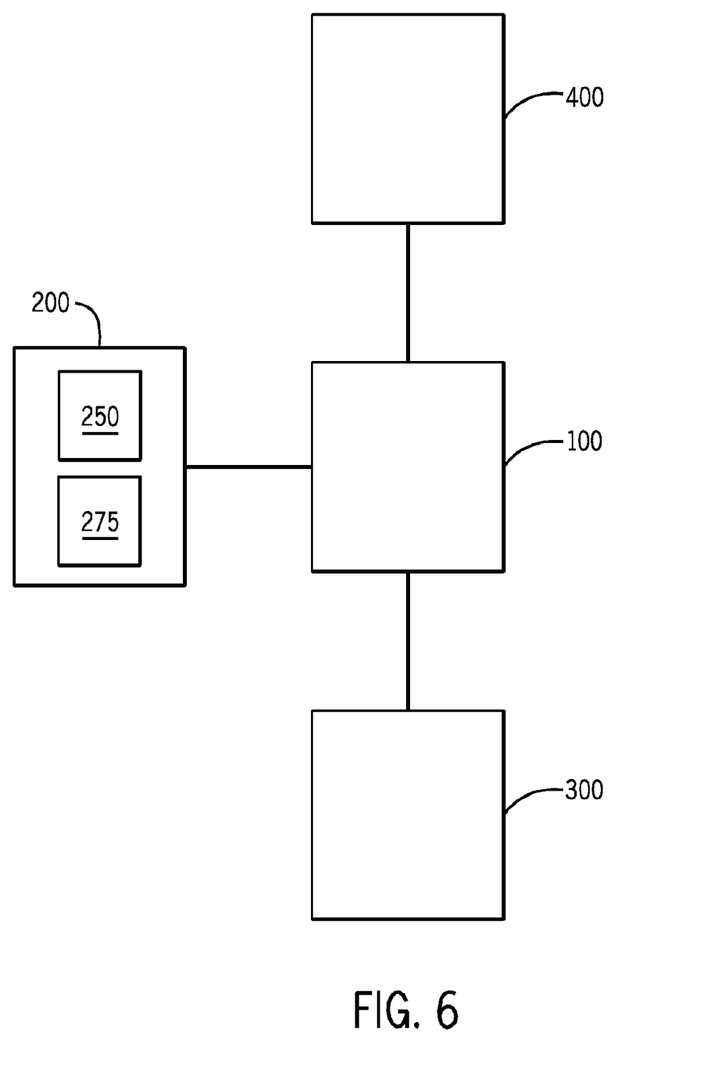
FIG. 6 shows a computer system for implementing the systems and methods described herein.

In another form of the invention, the systems and methods described herein can be implemented by a computer 200 shown in FIG. 6. The computer 200 includes conventional RAM and ROM components 250 and 275 respectively and executes stored computer software for carrying out the method of the invention. Therefore, for example, the system 100 performing particle fractionation is functionalized by the computer 200 implementing the methods of the invention via the computer software. A commercial system 300 can provide selected input material for fractionation by the system 100 for downstream commercial processing by a component 400.

Therefore, as described in the previous paragraph, this method and system can be implemented by a non-transitory computer readable medium (or storage medium such as the RAM 250 or ROM 275) including instructions that are accessible by a hardware processing arrangement thereon for controlled fractionation of particles having a plurality of attributes, wherein, when the processing arrangement executes the instructions, the processing arrangement (such as the computer 200), is configured to generate a hologram to produce an array of optical traps having a selected array lattice constant, the selected lattice constant established to deflect the particles in accordance with at least one of the plurality of attributes of the particles.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method for controlled fractionation of particles having particle attributes, comprising:
providing a sample having a plurality of particles;
preparing a uniform array of optical traps having a selected array lattice constant;
inputting the plurality of particles to the uniform array of optical traps at a driving direction angle $\phi_\tau$; and
separating the plurality of particles along different directions $\Theta_v$ based on selected variable ones of the particle attributes.

2. The method as defined in claim 1 wherein the variable ones of the particle attributes include at least one of a first attribute wherein a first particle having the first attribute is undeflected through the array of optical traps and another attribute wherein another particle having the another attribute is deflected along a direction $\phi_1$, within a range $\Delta\Theta v_1$.

3. The method as defined in claim 2 wherein the first attribute comprises being of a size too small to be deflected, thereby continuing along the driving direction angle $\Theta_v$.

4. The method as defined in claim 2 wherein the another attribute comprises being of a larger particle size and deflected along the direction $\phi_1$ within the range $\Delta\Theta v_1$.

5. The method as defined in claim 2 wherein the another attribute comprises being of another larger particle size and deflected along a direction $\phi_2$ within a range $\Delta\Theta v_2$.

6. The method as defined in claim 2 wherein the another attribute comprises an index of refraction $n_p$ causing deflection along a direction $\phi_3$ within a range $\Delta\Theta v_3$.

7. The method as defined in claim 6 wherein the index of refraction consists of a complex index of refraction.

8. The method as defined in claim 1 wherein the selected array lattice constant is modified to adjust the direction $\Theta_v$.

9. The method as defined in claim 1 wherein the driving direction angle $\phi_\tau$ is modified to adjust the direction $\Theta_v$.

10. The method as defined in claim 7 wherein the complex index of refraction comprises, $$n_v(a_p)n_m\sqrt{\frac{A(a_p)+2B_v(0)}{A(a_p)-B_v(\Theta)}}, \text{ where}$$

$$A(a_p) = \left(\frac{a_p}{b}\right)^2\left(\frac{b}{\sigma_p}\right)^3\exp\left(-\frac{b^2}{8\sigma_p^2}\right)$$

$$B_v(\Theta) = \frac{\sqrt{e}}{2}\frac{6\pi\eta vc}{n_m P}b\sin(\Theta-\Theta_v)$$

where $\eta$=viscosity, $v$=particle velocity, b=array lattice constant, c-speed of light in vacuum and P=laser power
wherein the particles satisfying, $n_p \geq n_p(a_p)$ are locked-in to a direction at angle $\Theta_v$ and these particles with $n_p \geq n_p(a_p)$ escape.

11. The method as defined in claim 1 further including the step of providing a computer and non-transitory computer readable medium for executing software to control the array of optical traps.

12. A system for controlled fractionation of particles having a plurality of attributes, comprising:
an array of optical traps having a selected array lattice constant, the selected array lattice constant established to deflect the particles in accordance with at least one of the plurality of attributes of the particles.

13. The system as defined in claim 12 further including a computer, embedded computer software and a non-transitory medium for cooperatively performing the step of designing a uniform array of optical traps.

14. The system as defined in claim 12 wherein the lattice array constant includes at least one value.

15. The system as defined in claim 12 wherein the array lattice constant includes at least two different values, one array lattice constant value disposed along one direction of the array and another array lattice constant disposed along a different direction of the array.

16. The system as defined in claim 12 wherein the array of optical traps has a selected effective optical and potential energy character that interacts with a particle index of refraction to thereby cause an associated deflection.

17. The system as defined in claim 12 wherein the array of optical traps has a selected effective optical and potential energy character that interacts with a particle attribute to thereby cause an associated deflection.

18. The system as defined in claim 17 wherein the optical character and potential energy character includes a selected potential energy depth for the optical traps.

19. The system as defined in claim 13 wherein the computer executes the computer software to control the array of optical traps.

20. A non-transitory computer readable medium including instructions thereon for controlled fractionation of particles having a plurality of attributes wherein the medium and the instructions are accessible by a hardware processing arrangement, wherein, when the hardware processing arrangement executes the instructions, the processing arrangement is configured to generate a hologram to produce an array of optical traps having a selected array lattice constant, the selected lattice constant established to deflect the particles in accordance with at least one of the plurality of attributes of the particles.

* * * * *